US00PP10646P

United States Patent [19]

Holtkamp, Sr.

[11] Patent Number: Plant 10,646

[45] Date of Patent: Oct. 13, 1998

[54] AFRICAN VIOLET PLANT NAMED MICHIKO

[75] Inventor: Reinhold Holtkamp, Sr., Rees-Haffen, Germany

[73] Assignee: International Plant Breeding A.G., Bern, Switzerland

[21] Appl. No.: 799,016

[22] Filed: Feb. 7, 1997

[51] Int. Cl.[6] ..... A01H 5/00

[52] U.S. Cl. ..... Plt./69.2

[58] Field of Search ..... Plt./69.2

[56] References Cited

PUBLICATIONS

UPOV CD ROM, German PBR USV 00424, Saintpaulia named Michiko, 1992.

*Primary Examiner*—James R. Feyrer
*Assistant Examiner*—Melissa L. Kimball
*Attorney, Agent, or Firm*—Foley & Lardner

[57] ABSTRACT

A new and distinct cultivar of African violet named Michiko, as described and illustrated, and particularly characterized by its single violet-shaped light blue/white wash bi-colored flowers which have a white background and light blue color radiating from the white center into the petals and fading into lighter shades towards the edges; fine white, slightly wavy line on the bloom edges; strong, upright flower stems that curve slightly toward the center to form a compact bouquet above the leaves; medium green, oval to heart-shaped leaves; profuse flowering, vigorous and compact growth habit, flowering 9–10 weeks after potting, and by its long lasting and non-dropping flowers.

1 Drawing Sheet

The present invention comprises a new and distinct cultivar of African violet plant, botanically known as *Saintpaulia ionantha,* and hereinafter referred to by the cultivar name.

The new cultivar was referred to during the breeding and selection process by the designation 930/13 and is a product of a planned breeding proram. The new cultivar was originated from a cross made by me in the controlled breeding program in Haffen, Federal Republic of Germany. The female, or seed parent was a cultivar designated 253. The male, or pollen parent was a cultivar designated 930.

Michiko was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Michiko has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Michiko, which in combination distinguish this African violet as a new and distinct cultivar:

1) Strong, upright flower stems curving slightly toward the center.

2) Single violet-shaped bi-colored light blue-white wash flowers.

3) Profuse flowering.

4) Each plant carries 10–12 and more upright flower stems each of which carries 10–12 and more flowers.

5) Long lasting, non-dropping flowers.

6) Vigorous and compact grower.

7) Plant saleable 9–10 weeks after potting.

8) Seed capsules push slightly through.

9) Medium green, oval to heart-shaped leaves.

10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Color Chart (R.H.S), except where general colors of ordinary significance are referred to. Color values were taken under natural sunlight conditions at approximately 12 p.m. in Nashville, Tenn.

Botanical classification: *Saintpaulia ionantha*, Ramat., c.v. Michiko.

Parentage:

*Male parent.*—930.

*Female parent.*—253.

Propagation: The new cultivar holds its distinguishing characteristics through successive propagations by leaf cuttings.

Plant: From 8 cm to 10 cm tall when grown in pots, and 24–27 cm in diameter when fully grown.

*Leaves.*—General form: Oval to heart-shaped. Diameter: 50–60 mm wide and 60–70 mm long. Texture: Velvety. Aspect: Slightly serrated, hairy, slightly shiny. Veins: Upperside: visible; underside: well pronounced, light green, shiny. Color (upperside): Yellow-Green Group147 A. Color (underside): Greyed-Green Group 194 C to D; young leaves are Greyed-Purple Group 186 C.

*Petiole.*—Strong, green with brownish touch, hairy.

*Flowers.*—Buds: Bell-shaped, light green with bluish streaks, 5–7 mm just before opening. Sepals: Five (5). Color: Green with brownish touch. Calyx: Shape: Funnel-shaped. Aspect: Spear-shaped, hairy. Peduncle: Character: Strong upright, hairy. Color: Green with brownish touch.

*Individual flowers.*—Size: 34–38 mm. Shape: Single violet-shaped with slightly wavy edges. Color (upperside): White background with Violet-Blue Group 91 A radiating into the petals and fading into B, C and D. Under cooler temperatures and more intensive lighting, the light blue tends to intensify. Color (underside): Violet-Blue Group 91 D with streaks of 91 A to B. Borne: Each flower stem carries 10–12 and more flowers on strong, upright peduncles that are free standing above the leaves, thereby forming a compact bouquet. Flowering habit: Flowers 9–10 weeks after potting.

*Reproductive organs.*—Stamens: Two (2). Anthers: 2 composed of 4 anther cells, seed capsules push slightly through. Filaments: Yellowish white, 3–4 mm long. Pollen color: Yellow Group 7 A. Styles: 7–8 mm long, white, base of ovary light green and hairy.

*Roots.*—Normally developed, white when young, turning slightly brownish when older.

Disease resistance: Up to date, Michiko has shown very good resistance to all major violet diseases.

General observations

Michiko is an attractive cultivar due to its light blue-white wash bi-colored flowers. The background color is white and light blue radiates from the white center into the petals (especially the three large ones) and fades to lighter shades toward the edges which have a fine white, slightly wavy line. A tight bouquet of flowers free standing above the leaves develops after 9–10 weeks. Each of the 10–12 and more strong flower stems carries 10–12 and more single voilet-shaped flowers. Medium green, oval to heart-shaped leaves surround the flower bouquet. The flowers are long-lasting and non-dropping and the seed capsules push slightly through.

I claim:

1. A new and distinct cultivar of African violet named Michiko, as described and illustrated, and particularly characterized by its single violet-shaped light blue/white wash bi-colored flowers which have a white background and light blue color radiating from the white center into the petals and fading into lighter shades towards the edges; fine white, slightly wavy line on the bloom edges; strong, upright flower stems that curve slightly toward the center to form a compact bouquet above the leaves; medium green, oval to heart-shaped leaves; profuse flowering; vigorous and compact growth habit; flowering 9–10 weeks after potting, and by its long lasting and non-dropping flowers.

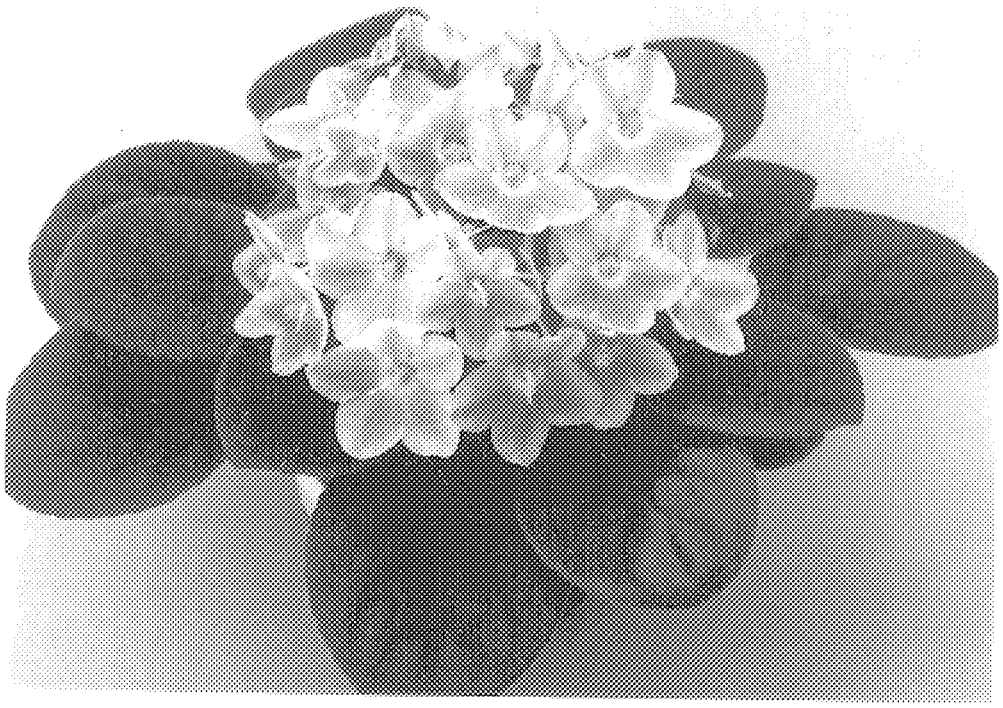

* * * * *